United States Patent
Mou et al.

(10) Patent No.: US 12,280,187 B2
(45) Date of Patent: Apr. 22, 2025

(54) BREAST PUMP

(71) Applicant: MICROJET TECHNOLOGY CO., LTD., Hsinchu (TW)

(72) Inventors: Hao-Jan Mou, Hsinchu (TW);
Ching-Sung Lin, Hsinchu (TW);
Chih-Kai Chen, Hsinchu (TW);
Wen-Yang Yang, Hsinchu (TW);
Yung-Lung Han, Hsinchu (TW);
Chi-Feng Huang, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 448 days.

(21) Appl. No.: 17/577,437

(22) Filed: Jan. 18, 2022

(65) Prior Publication Data
US 2023/0211055 A1  Jul. 6, 2023

(30) Foreign Application Priority Data
Jan. 4, 2022  (TW) .................................. 111100204

(51) Int. Cl.
*A61M 1/06*  (2006.01)
(52) U.S. Cl.
CPC ............ *A61M 1/067* (2021.05); *A61M 1/064* (2014.02); *A61M 1/06935* (2021.05); *A61M 1/0697* (2021.05); *A61M 2205/3331* (2013.01)
(58) Field of Classification Search
None
See application file for complete search history.

(56) References Cited

U.S. PATENT DOCUMENTS

| | | | |
|---|---|---|---|
| 2002/0183719 A1* | 12/2002 | Morton | A61B 5/6834 604/74 |
| 2002/0198489 A1 | 12/2002 | Silver et al. | |
| 2006/0270973 A1* | 11/2006 | Chu | A61M 1/067 604/74 |
| 2008/0208116 A1* | 8/2008 | Dao | A61M 1/064 604/74 |
| 2010/0094078 A1* | 4/2010 | Weston | A61M 1/0693 604/74 |
| 2015/0065994 A1* | 3/2015 | Fridman | A61M 1/0697 604/74 |
| 2016/0206794 A1* | 7/2016 | Makower | A61M 1/067 |

(Continued)

FOREIGN PATENT DOCUMENTS

| | | |
|---|---|---|
| CN | 102068721 A | 5/2011 |
| CN | 103272292 A | 9/2013 |

(Continued)

*Primary Examiner* — Courtney B Fredrickson
(74) *Attorney, Agent, or Firm* — Birch, Stewart, Kolasch & Birch, LLP

(57) ABSTRACT

A breast pump includes a main body and a breast milk suctioning shield. The main body has an accommodation space. The breast milk suctioning shield is assembled in the accommodation space and detachably connected to the main body. A front end of the breast milk suctioning shield has a breast shielding portion, and a nipple passage extends from a rear end of a center portion of the breast shielding portion. One or more deformable members are assembled with an annular connection portion between the breast shielding portion and the nipple passage, and the deformable member is controlled to be inflated or deflated by a first air pump.

21 Claims, 6 Drawing Sheets

(56) References Cited

U.S. PATENT DOCUMENTS

| | | | |
|---|---|---|---|
| 2016/0220743 A1* | 8/2016 | Guthrie | G06F 3/0482 |
| 2017/0112983 A1* | 4/2017 | Thorne | A61M 1/067 |
| 2017/0136160 A1* | 5/2017 | Barral | A61M 1/0693 |
| 2018/0110906 A1* | 4/2018 | Barack | A61M 1/06935 |
| 2018/0126052 A1* | 5/2018 | Looney | A61M 1/06 |
| 2018/0193539 A1 | 7/2018 | Quackenbush | |
| 2018/0361040 A1* | 12/2018 | O'Toole | A61M 1/0697 |
| 2020/0078503 A1* | 3/2020 | Bartlett | A61M 1/062 |
| 2021/0069391 A1* | 3/2021 | Quackenbush | A61M 1/064 |
| 2021/0205513 A1 | 7/2021 | O'Toole et al. | |

FOREIGN PATENT DOCUMENTS

| | | |
|---|---|---|
| CN | 104587543 A | 5/2015 |
| CN | 210812921 U | 6/2020 |
| JP | 2020-523179 A | 8/2020 |
| TW | 201811381 A | 4/2018 |

\* cited by examiner

BREAST PUMP

CROSS-REFERENCE TO RELATED APPLICATION

This non-provisional application claims priority under 35 U.S.C. § 119(a) to patent application Ser. No. 11/100,204 in Taiwan, R.O.C. on Jan. 4, 2022, the entire contents of which are hereby incorporated by reference.

BACKGROUND

Technical Field

The present disclosure relates to a breast milk collecting device which is suitable for breast-feeding and is hands-free, in particular, to a breast pump suitable for wearing.

Related Art

Passive breast milk collection is an area of breastfeeding that is worth to be addressed. Passive breast milk release is originated from the natural "breast milk releasing" phenomenon occurring to a woman upon an infant "sucks" the breast of the woman for breast-feeding. When the breast is stimulated to release the breast milk by applying a suctioning force to the breast, owing to this "lactation phenomenon", before collecting, a plenty of breast milk that can be collected into the feeding bottles to feed the infants is wasted by most mothers who adopt breast-feeding. Therefore, a novel breast milk collecting device is required to collect the breast milk passively released from the breast for subsequent feeding. Hence, a breast milk collecting device which is hands-free, hiddenable, and ergonomic is provided in this invention, the breast milk collecting device is a breast pump that does not need to be operated manually and is easy to be placed, disassembled, cleaned, and reassembled. Moreover, the user can place the breast pump under the daily cloth without taking off cloth or wearing complicated and apparent holding straps to execute a hands-free breast milk collection procedure.

Furthermore, it is understood that, the commercial breast pump merely performs a breast milk suctioning operation through continuously applying a negative-pressure on the breast, and thus is devoid of an operation mode corresponding to the "lactation phenomenon" of a woman's breast. As a result, the conventional breast pump can just suction the breast milk currently secreted by the breast, and no further breast milk can be suctioned from the breast by the conventional breast pump after the conventional breast pump performs the breast milk suctioning operation to a woman's breast for a while. Thereafter, the woman conducting breast-feeding will feel pain and uncomfortable at her breast as the breast pump continuously suctions her breast. Hence, the conventional breast pump fails to mimic the natural "lactation phenomenon" occurred when an infant "sucks" the breast of the woman and allow the pituitary gland of the woman to be stimulated to secret oxytocin to allow the mammary gland of the breast to produce the breast milk. Consequently, how to provide a breast pump capable of performing intermittent and automatic suctioning operation to mimic the natural "lactation phenomenon" is an issue of concern to be developed in this invention.

SUMMARY

One object of the present disclosure is to provide a breast pump, wherein a first detector or a second detector of the breast pump is provided to determine whether the breast milk is released from the mammary gland of the breast and control the operation of the air pump to inflate and deflate at least one deformable member alternately. Moreover, a non-deformable supporting member is provided corresponding to the at least one deformable member, and the breast of the woman can be touched, pressed, and held together by the non-deformable supporting member and the at least one deformable member to mimic infants' suckling behaviors, so as to allow the lactation phenomenon to occur, and the pituitary gland of the woman is stimulated to secret prolatine or oxytocin and allow the mammary gland of the breast to produce the breast milk. On the other hand, detections of the first detector and the second detector allow the breast pump to adjust the negative-pressure suctioning force automatically and control the operation frequency through turning on or off the air pump, thereby achieving an intermittent and automatic operation for suctioning the breast milk.

To achieve the object mentioned above, in one embodiment of the present disclosure, a breast pump is provided to be placed at a breast of a user for collecting breast milk. The breast pump includes a main body and a breast milk suctioning shield. The main body has an accommodation space. The breast milk suctioning shield is assembled in the accommodation space and detachably connected to the main body. A front end of the breast milk suctioning shield has a breast shielding portion, and a nipple passage extends from a rear end of a center portion of the breast shielding portion. At least one deformable member is assembled with an annular connection portion between the breast shielding portion and the nipple passage, and the at least one deformable member is controlled to be inflated or deflated by a first air pump.

BRIEF DESCRIPTION OF THE DRAWINGS

The disclosure will become more fully understood from the detailed description given herein below, for illustration only and thus not limitative of the disclosure, wherein.

DETAILED DESCRIPTION

Figure 1A:
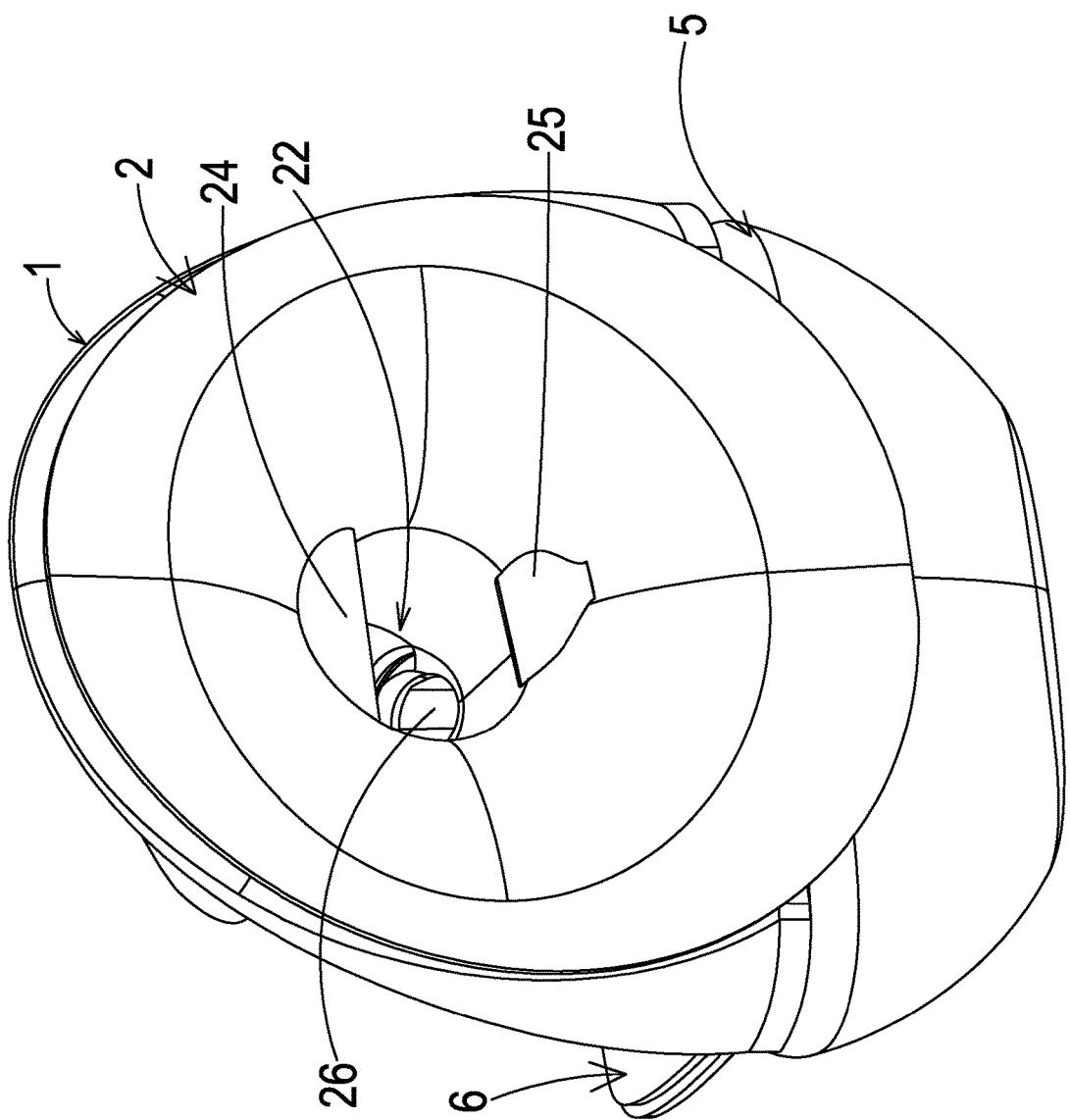
FIG. 1A illustrates a schematic perspective view of a breast pump according to an exemplary embodiment of the present disclosure.

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Please refer to FIG. 1A to FIG. 1F, a breast pump is provided. In one embodiment, the breast pump includes a main body 1, a breast milk suctioning shield 2, a first air pump 3, a duckbill valve 4, a breast milk container 5, a connector component 6, at least one second air pump 7, and a flexible separation film 8.

Figure 1B:
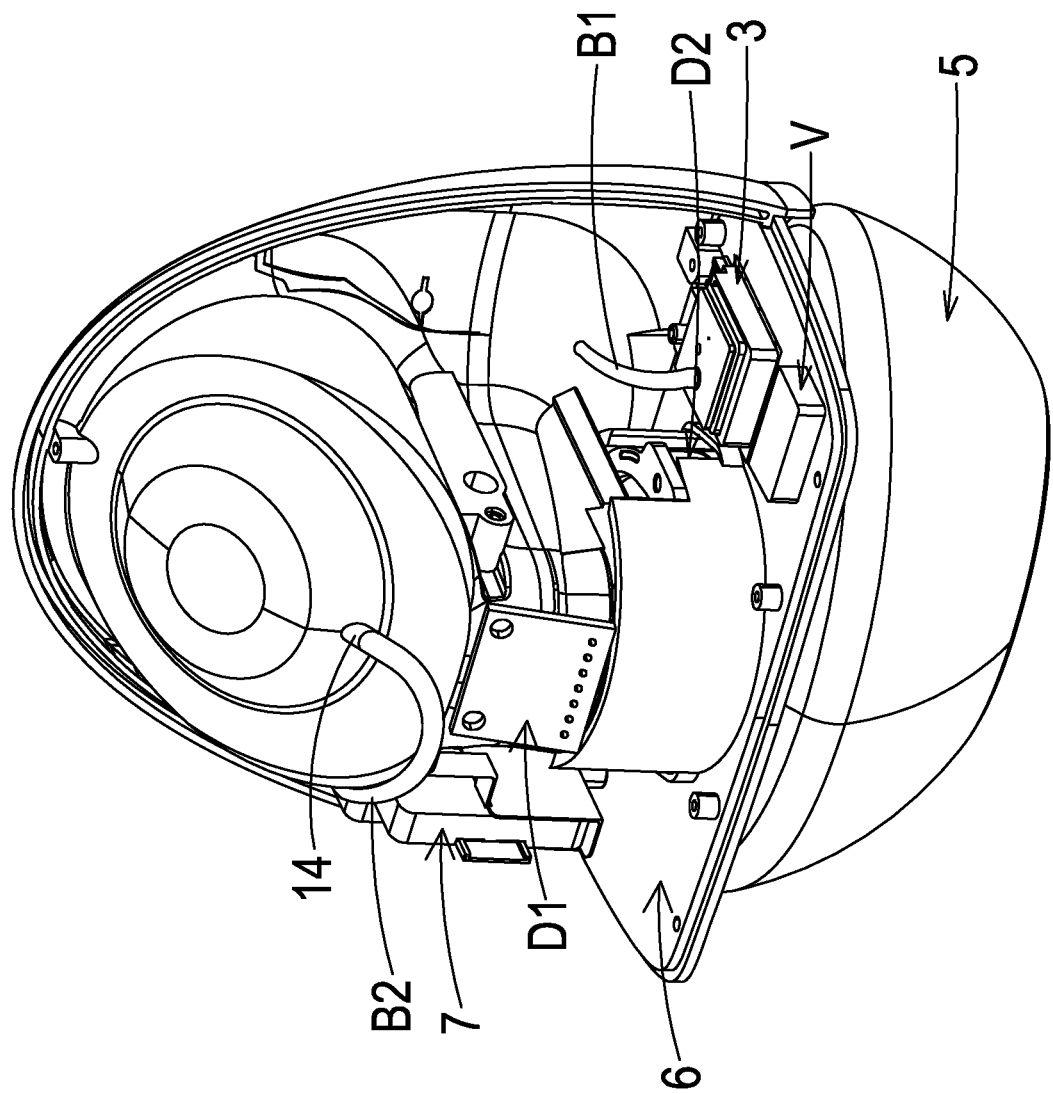
FIG. 1B illustrates a schematic perspective view of the breast pump of the exemplary embodiment of the present disclosure from another view angle.
Figure 1C:
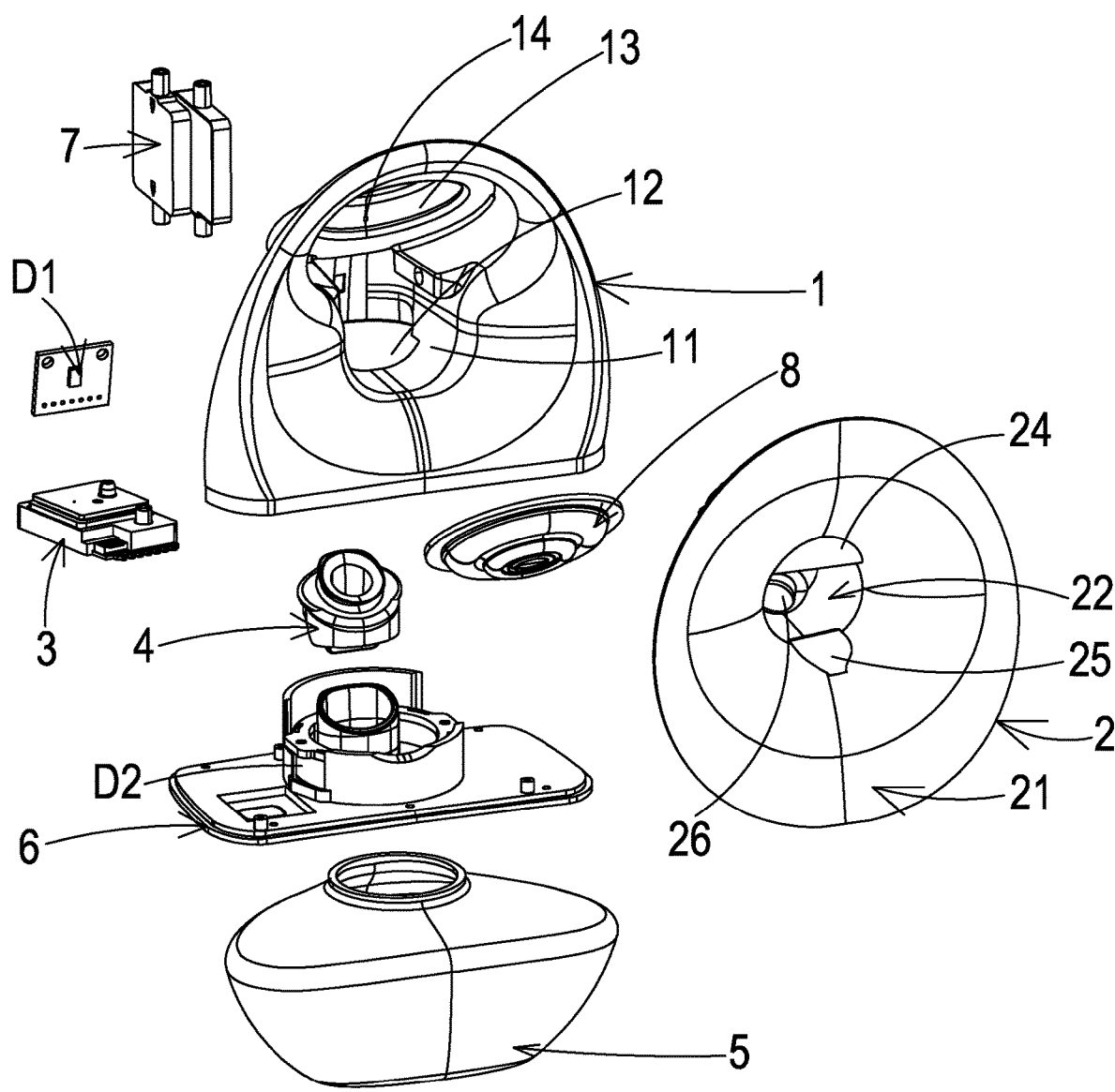
FIG. 1C illustrates an exploded view of the breast pump of another exemplary embodiment of the present disclosure.
Figure 1D:
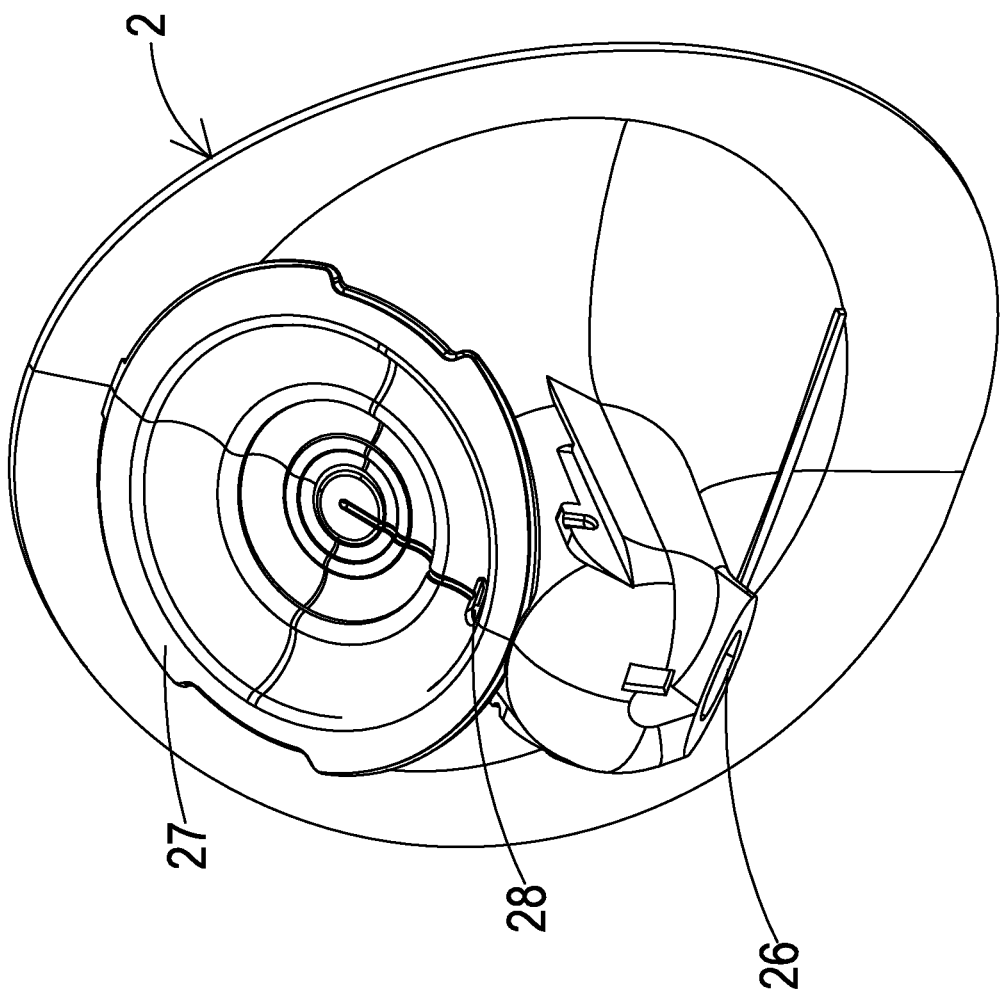
FIG. 1D illustrates a schematic view of a breast milk suctioning shield of the breast pump of the exemplary embodiment of the present disclosure.
Figure 1E:
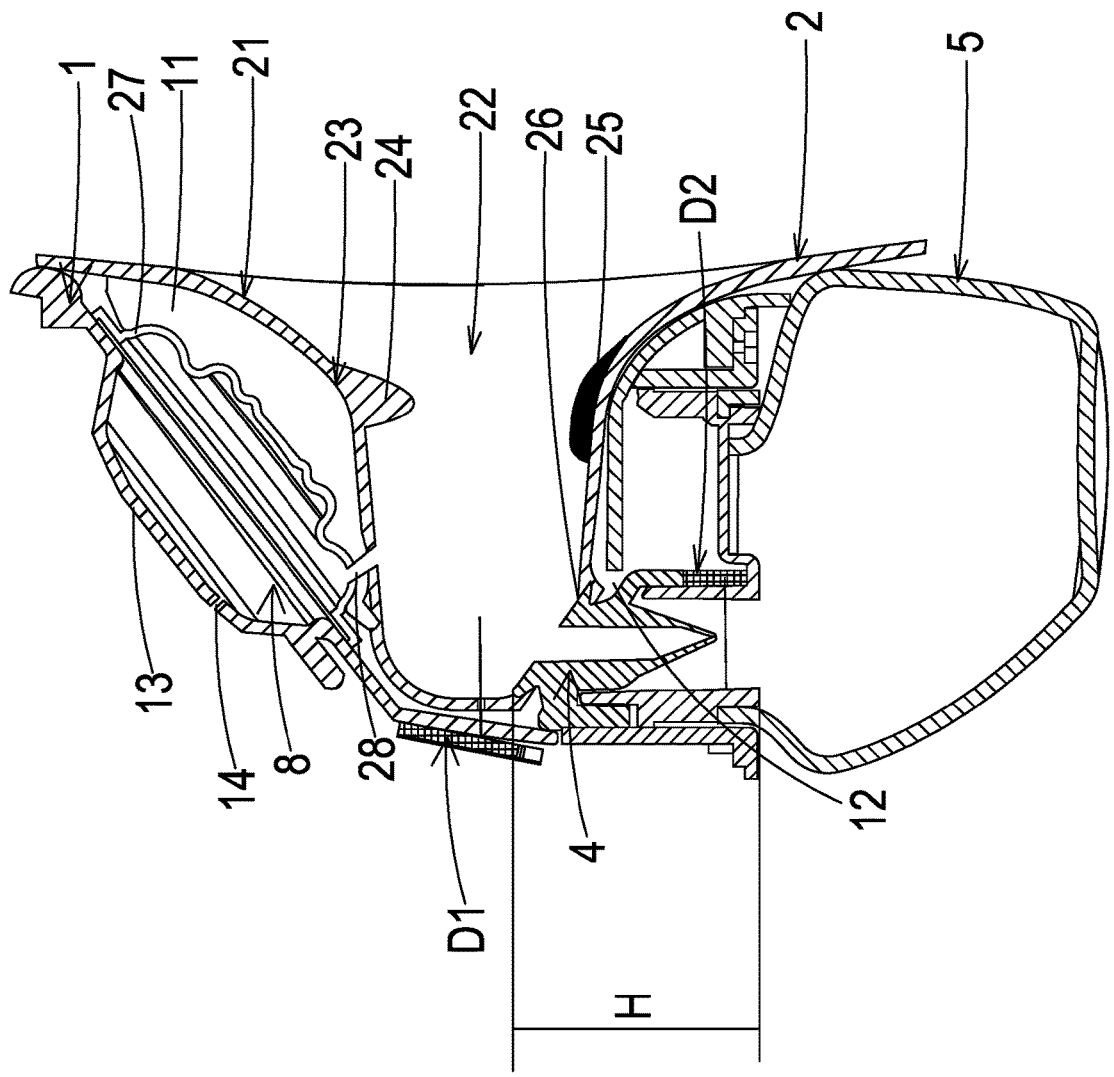
FIG. 1E illustrates a cross-sectional view of the breast pump of the exemplary embodiment of the present disclosure.

As shown in FIG. 1B, FIG. 1C, and FIG. 1E, the main body 1 has an accommodation space 11, and the accommodation space 11 includes an opening 12 and a separation film recess 13.

As shown in FIG. 1B, FIG. 1C, and FIG. 1E, the breast milk suctioning shield 2 is transparent and is made of a rigid material or a semi-rigid material, the breast milk suctioning shield 2 is assembled in the accommodation space 11 of the main body 1, and the breast milk suctioning shield 2 is detachably connected to the main body 1. A front end of the breast milk suctioning shield 2 has a breast shielding portion 21, and a nipple passage 22 extends from a rear end of a center portion of the breast shielding portion 21. At least one deformable member 25 is assembled with an annular connection portion 23 between the breast shielding portion 21 and the nipple passage 22. In one embodiment, the breast milk suctioning shield 2 further includes a non-deformable supporting member 24 placed at a location corresponding to the at least one deformable member 25 in the annular connection portion 23. The at least one deformable member 25 is controlled to be inflated or deflated by the first air pump 3, and the first air pump 3 is connected to the at least one deformable member 25 through a first pipeline B1 (as shown in FIG. 1B). In one embodiment, the breast pump includes a plurality of the first air pumps 3, and the first air pumps 3 are assembled in the first pipeline B1 in a series-connection manner or a parallel-connection manner, but not limited thereto. In one embodiment, one deformable member 25 and one non-deformable supporting member 24 opposite to the deformable member 25 are assembled in the annular connection portion 23 between the breast shielding portion 21 and the nipple passage 22, but not limited thereto; the number of the deformable member 25 and the non-deformable supporting member 24 can be adjusted according to actual requirements. The first air pump 3 is enabled to inflate the deformable member 25, and the deformable member 25 is automatically deflated when the first air pump 3 is disabled. Therefore, when the first air pump 3 is enabled, the deformable member 25 is inflated by a gas; when the first air pump 3 is disabled, the gas in the deformable member 25 flows back to the first air pump 3 through the first pipeline B1, so that the deformable member 25 can be deflated automatically. In one embodiment, the first air pump 3 is a piezoelectric pump; alternatively, in another embodiment, the first air pump 3 is an electric pump that may be a motor, a pneumatic pump, an electromagnetic pump, or other power-driven pumping device, but not limited thereto. In one embodiment, the breast shield portion 21 is made of a flexible material and is adapted to be closely attached to the breast of the user, but not limited thereto. In one embodiment, the non-deformable supporting member 24 is made of a semi-rigid material and may be a flange structure, but not limited thereto. In one embodiment, the deformable member 25 is made of a flexible material which is capable of being inflated and expanded or deflated and contracted. Alternatively, in one embodiment, the deformable member 25 may be made of silicone rubber or thermoplastic polyurethane (TPU). In one embodiment, the deformable member 25 is an air bag and is capable of being inflated and expanded or deflated and contracted, but not limited thereto.

Further, as shown in FIG. 1C and FIG. 1E, the nipple passage 22 of the breast milk suctioning shield 2 has a breast milk outlet 26 corresponding to the opening 12 of the main body 1. Moreover, the breast milk container 5 is assembled at a bottom portion of the main body 1, and a connector component 6 is disposed between the bottom portion of the main body 1 and the breast milk container 5, so that the breast milk container 5 is assembled on the bottom portion of the main body 1 corresponding to the connector component 6 through the connector component 6, and the breast milk container 5 is corresponding to the breast milk outlet 26 of the nipple passage 22 to form an outflow passage H.

Figure 1F:
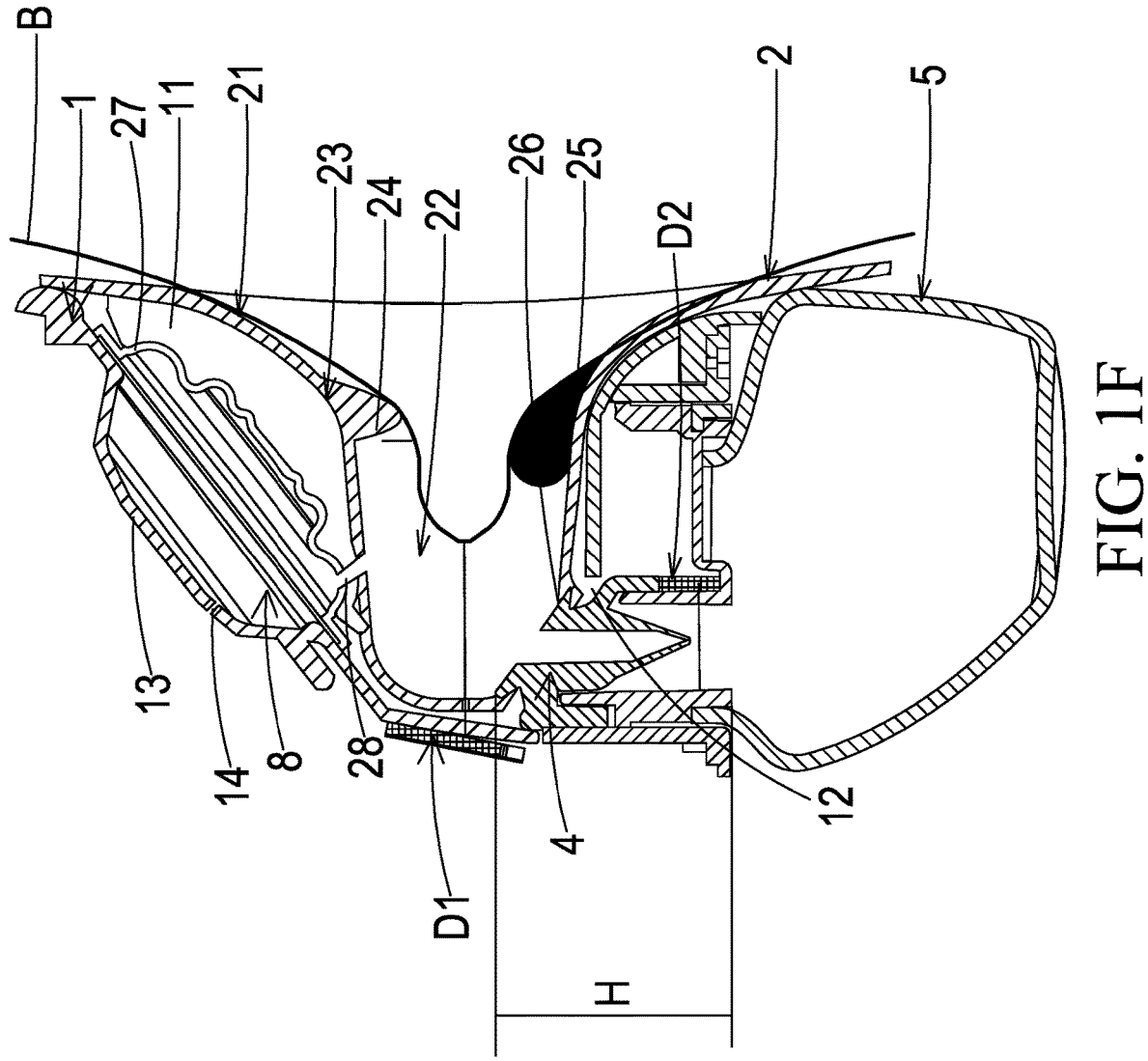
FIG. 1F illustrates a cross-sectional view showing the breast milk suctioning operation of the breast pump of the exemplary embodiment of the present disclosure.

As shown in FIG. 1E and FIG. 1F, the duckbill valve 4 is disposed at the breast milk outlet 26 of the nipple passage 22. When the breast milk is inside the nipple passage 22, the breast milk flows into the duckbill valve 4 through the breast milk outlet 26, so that the duckbill valve 4 is automatically opened to allow the breast milk to flow into the outflow passage H smoothly to be collected in the breast milk container 5. On the other hand, when no breast milk flows into the duckbill valve 4, the duckbill valve 4 is closed to prevent the breast milk in the breast milk container 5 from flowing back to the breast milk outlet 26 of the nipple passage 22.

Further, as shown in FIG. 1B, FIG. 1C, FIG. 1D, and FIG. 1E, the separation film recess 13 is in communication with an air port 14, and the air port 14 is connected to a second air pump 7 outside the accommodation space 11 through a second pipeline B2 (as shown in FIG. 1B). Moreover, a separation film base 27 is assembled on an outer portion of the breast shielding portion 21 of the breast milk suctioning shield 2, and the separation film base 27 has a negative-pressure port 28 in communication with the nipple passage 22. The flexible separation film 8 is assembled and positioned in the separation film base 27, and the breast milk suctioning shield 2 is assembled in the accommodation space 11 of the main body 1. The separation film base 27 is connected to the separation film recess 13, so that the flexible separation film 8 is completely sealed and positioned between the separation film base 27 and the separation film recess 13. Furthermore, the air port 14 of the separation film recess 13 is connected to the second air pump 7 through the second pipeline B2. A negative-pressure suctioning force is generated and transmitted to the separation film recess 13 through enabling the second air pump 7, the flexible separation film 8 between the separation film base 27 and the separation film recess 13 is deformed and generates the negative-pressure suctioning force in the separation film base 27 which results in the negative-pressure suctioning force in the nipple passage 22 through the negative-pressure port 28. Hence, when the breast B is placed on the nipple passage 22, the breast B is suctioned by the negative-pressure suctioning force, so as to achieve the breast milk suctioning operation of the breast pump. In one embodiment, the breast pump includes a plurality of the second air pumps 7, and the second air pumps 7 are assembled in the second pipeline B2 in a series-connection manner or a parallel-connection manner, but not limited thereto. In one embodiment, the second air pump 7 is a piezoelectric pump; alternatively, in another one embodiment, the second air pump 7 is an electric pump that may be a motor, a pneumatic pump, an electromagnetic pump, or other power-driven pumping device, but not limited thereto.

Moreover, as shown in FIG. 1E and FIG. 1F, the breast shielding portion 21 of the breast milk suctioning shield 2 is adapted to be placed at the breast B of the user with the nipple of the breast B being placed in the nipple passage 22. Therefore, the first air pump 3 is enabled to inflate and deflate the deformable member 25 alternately, so as to press and touch the breast B. Hence, the breast pump can mimic the sucking or touching behaviors of an infant (also including licking and sucking) to the breast B. Alternatively, in one embodiment, the first air pump 3 is enabled to inflate and deflate the deformable member 25 alternately to press and touch the breast B, and the breast B is further touched, pressed, and held together by the non-deformable supporting member 24 and the deformable member 25. Hence, the breast pump can properly mimic the "sucking" or "licking" behaviors of an infant to the breast B, so as to induce the lactation phenomenon and stimulate the pituitary gland of the user to secret prolatine or oxytocin and allow the mammary gland of the breast B to produce the breast milk.

Moreover, as shown in FIG. 1E and FIG. 1F, in one embodiment, a first detector D1 is disposed at a rear portion of the nipple passage 22 of the breast milk suctioning shield 2, the first detector D1 detects whether the breast B ejects the breast milk and determines whether the breast milk is released from the mammary gland of the breast B. In another embodiment, a second detector D2 is disposed on the periphery of the outflow passage H, and the second detector D2 detects whether the breast B ejects the breast milk and determines whether the breast milk is released from the mammary gland of the breast B. Specifically, the first detector D1 or the second detector D2 detects none of the breast milk inside the nipple passage 22 or none of the breast milk flowing through the outflow passage H of the breast milk container to determine whether the breast milk is released from the mammary gland of the breast B.

When the first detector D1 or the second detector D2 detects and determines that the breast milk is not released from the mammary gland of the breast B, the first detector D1 or the second detector D2 enables the first air pump 3 to inflate and deflate the deformable member 25 alternately to press and touch the breast B. Hence, through alternate inflations and deflations of the deformable member 25, the breast pump can mimic the "licking" and "sucking" behaviors of an infant to the breast B. Consequently, the breast B is stimulated to eject the breast milk. In another embodiment, the first air pump 3 is enabled to inflate and deflate the deformable member 25 alternately to press and touch the breast B, and the breast B is further touched, pressed, and held together by the non-deformable supporting member 24 and the deformable member 25 to properly mimic the "licking" and "sucking" behaviors of an infant to the breast B. Consequently, the breast B is stimulated to eject the breast milk.

As mentioned, according to one or some embodiments of the present disclosure, the breast pump provides an intermittent and automatic operation for suctioning the breast milk. The first detector D1 and/or the second detector D2 (the first detector D1, the second detector D2, and both the first detector D1 and the second detector D2) of the breast pump is provided to determine whether the breast milk is released from the mammary gland of the breast B and control the operation of the first air pump 3 to inflate and deflate the at least one deformable member 25 alternately. Moreover, through disposing the non-deformable supporting member 24 corresponding to the deformable member 25, the breast B of the user can be touched, pressed, and held together by the non-deformable supporting member 24 and the deformable member 25 to mimic infants' suckling behaviors, so as to induce the lactation phenomenon and stimulate the pituitary gland of the user to secret prolatine or oxytocin and allow the mammary gland of the breast B to produce the breast milk. On the other hand, detections of the first detector D1 and/or the second detector D2 allow the breast pump to adjust the negative-pressure suctioning force automatically and control the operation frequency through turning on or off the second air pump 7, thereby achieving an intermittent and automatic operation for suctioning the breast milk. In other words, in this embodiment, when the first detector D1 and/or the second detector D2 detects that the breast milk is not released from the mammary gland of the breast B, the negative-pressure suctioning force generated by the deformation of the flexible separation film 8 controlled by the second air pump 7 gradually decreases. Hence, the continuously suctioning operation is not continued when the breast milk is not released without leading to any pain or uncomfortable of the user. Further, the intermittent operation of the second air pump 7 is suspended and waiting for the restarting of the first air pump 3. Hence, the deformable member 25 of the breast pump of one or some embodiments of the present invention can be inflated and deflated alternately to press and touch the breast B, so as to mimic infants' suckling behaviors. Furthermore, the infants' suckling behaviors can also be mimicked through pressing and holding the breast B of the user by the deformable member 25 against the non-deformable supporting member 24. Therefore, during the breast milk suction operation, the pituitary gland of the user is stimulated to secret prolatine or oxytocin and allow the mammary gland of the breast B to produce the breast milk. Thereafter, the negative-pressure suctioning force is adjusted automatically through the operation of the second air pump 7, so as to achieve the intermittent and automatic operation for suctioning the breast milk through controlling the enablement and disablement of the second air pump 7. Therefore, the breast pump of one or some embodiments of this invention can provide a proper breast milk suction operation which can be performed automatically and intermittently to mimic infants' suckling behaviors without leading to any pain or uncomfortable of the user.

Moreover, in one embodiment, the breast pump further includes a sound recording device V, and the sound recording device V can record sounds of infant (e.g., the sounds of crying, laughing, or sucking). The sound of the user's infant can be recorded by the sound recording device during breast feeding, and the sound recording device V can replay the infant sound when the user uses the breast pump. Hence, in this embodiment, in addition to the intermittent and automatic operation for suctioning the breast milk, the user can also hear the infant sound to stimulate the pituitary gland of the user to secret prolatine or oxytocin and allow the mammary gland to produce the breast milk.

As mentioned above, according to one or some embodiments of the present disclosure, the present invention provides a breast pump to achieve the intermittent and automatic operation for suctioning the breast milk. Moreover, in some embodiments, a first detector and/or a second detector of the breast pump is provided to determine whether the breast milk is released from the mammary gland of the breast and control the operation of the air pump to inflate and deflate at least one deformable member alternately. Moreover, the deformable member is in combination with a non-deformable supporting member, and the breast of the woman can be touched, pressed, and held together by the non-deformable supporting member and the deformable member to mimic infants' suckling behaviors, so as to induce the lactation phenomenon and stimulate the pituitary gland of the woman to secret prolatine or oxytocin and allow the mammary gland of the breast to produce the breast milk. On the other hand, detections of the first detector and/or the second detector allow the breast pump to adjust the negative-pressure suctioning force automatically and control the enablement and disablement of the air pump, thereby achieving an intermittent and automatic operation for suctioning the breast milk.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A breast pump adapted to be placed at a mammary gland of a breast of a user to collect breast milk, wherein the breast pump comprises:
   a main body having an accommodation space;
   a breast milk suctioning shield assembled in the accommodation space and detachably connected to the main body, wherein a front end of the breast milk suctioning shield has a breast shielding portion, and a nipple passage extends from a rear end of a center portion of the breast shielding portion;
   at least one deformable member assembled with an annular connection portion located between the breast shielding portion and the nipple passage, and the at least one deformable member is controlled to be inflated and deflated by a first air pump;
   a breast milk container assembled with the main body; and
   a first detector disposed in the breast pump, wherein when the first detector detects none of the breast milk inside the nipple passage, a negative-pressure suctioning force generated by a second air pump decreases,
   wherein the first detector is disposed at a rear portion of the nipple passage of the breast milk suctioning shield to detect the breast milk inside the nipple passage; when the first detector detects none of the breast milk inside the nipple passage, the first detector enables the first air pump to inflate and deflate the at least one deformable member alternately to press and touch the breast.

2. The breast pump according to claim 1, wherein the first air pump is enabled to inflate the at least one deformable member, and the at least one deformable member is automatically deflated when the first air pump is disabled.

3. The breast pump according to claim 1, wherein the first air pump is a piezoelectric pump, an electric pump, or a combination thereof.

4. The breast pump according to claim 1, wherein the breast milk suctioning shield further comprises a non-deformable supporting member placed at a location corresponding to the at least one deformable member in the annular connection portion.

5. The breast pump according to claim 4, wherein the at least one deformable member is made of a flexible material.

6. The breast pump according to claim 4, wherein the at least one deformable member is made of silicone rubber, thermoplastic polyurethane (TPU), or a combination thereof.

7. The breast pump according to claim 4, wherein the at least one deformable member is an air bag.

8. The breast pump according to claim 1, wherein the breast shielding portion of the breast milk suctioning shield is adapted to be placed at the breast of the user, and the nipple passage is adapted to receive a nipple of the breast; the first air pump is enabled to inflate and deflate the at least one deformable member alternately to press and touch the breast, so as to allow the mammary gland of the breast to be stimulated to eject the breast milk.

9. The breast pump according to claim 1, wherein the first air pump is connected to the at least one deformable member through a first pipeline; when the first air pump is enabled, the at least one deformable member is inflated by a gas; when the first air pump is disabled, the gas in the at least one deformable member flows back to the first air pump through the first pipeline, so that the at least one deformable member is deflated automatically.

10. The breast pump according to claim 9, wherein the breast pump comprises a plurality of the first air pumps, and the first air pumps are assembled in the first pipeline in a series-connection manner or a parallel-connection manner.

11. The breast pump according to claim 1, wherein the breast milk suctioning shield is transparent and made of a rigid material or a semi-rigid material, and the breast shielding portion is made of a flexible material.

12. The breast pump according to claim 1, wherein the accommodation space of the main body comprises a separation film recess in communication with an air port, and the air port is connected to the second air pump outside the accommodation space through a second pipeline, so that the second air pump is enabled to generate the negative-pressure suctioning force to the separation film recess.

13. The breast pump according to claim 12, further comprising a flexible separation film, wherein a separation film base is assembled on an outer portion of the breast shielding portion of the breast milk suctioning shield, and the separation film base has a negative-pressure port in communication with the nipple passage; the flexible separation film is assembled and positioned in the separation film base, and the breast milk suctioning shield is assembled in the accommodation space of the main body; the separation film base is connected to the separation film recess, so that the flexible separation film is completely sealed and positioned between the separation film base and the separation film recess; the negative-pressure suctioning force is generated to the separation film recess by enabling the second air pump, the flexible separation film between the separation film base and the separation film recess is deformed and generate the negative-pressure suctioning force in the separation film base which results in the negative-pressure suctioning force in the nipple passage through the negative-pressure port, so that a breast milk suctioning operation of the breast pump is achieved.

14. The breast pump according to claim 12, wherein the breast pump comprises a plurality of the second air pumps, and the second air pumps are assembled in the second pipeline in a series-connection manner or a parallel-connection manner.

15. The breast pump according to claim 12, wherein the second air pump is a piezoelectric pump, an electric pump, or a combination thereof.

16. The breast pump according to claim 1, wherein the accommodation space of the main body has an opening, and the nipple passage of the breast milk suctioning shield has a breast milk outlet corresponding to the opening; a bottom portion of the main body is assembled with the breast milk container, and a connector component is disposed between the bottom portion of the main body and the breast milk container, so that the breast milk container is corresponding to the connector component and is assembled to the bottom portion of the main body through the connector component, and the breast milk container is corresponding to the breast milk container is corresponding to the breast milk outlet of the nipple passage to form an outflow passage.

17. The breast pump according to claim 16, wherein a duckbill valve is further disposed at the breast milk outlet of the nipple passage; when the breast milk flows into the nipple passage, the breast milk flows into the duckbill valve through the breast milk outlet, so that the duckbill valve is automatically opened to allow the breast milk to flow into the outflow passage smoothly to be collected in the breast milk container; when no breast milk flows into the duckbill valve, the duckbill valve is closed to prevent the breast milk in the breast milk container from flowing back to the breast milk outlet of the nipple passage.

18. The breast pump according to claim 16, wherein a second detector is disposed on a periphery of the outflow passage to detect the breast milk flowing through the outflow passage; when the second detector detects none of the breast milk flowing through the outflow passage, the second detector enables the first air pump to inflate and deflate the at least one deformable member alternately to press and touch the breast.

19. The breast pump according to claim 18, further comprising a non-deformable supporting member placed at a location corresponding to the at least one deformable member in the annular connection portion; wherein when the second detector detects none of the breast milk flowing through the outflow passage, the second detector enables the first air pump to inflate and deflate the at least one deformable member alternately to press and touch the breast.

20. The breast pump according to claim 1, further comprising a non-deformable supporting member placed at a location corresponding to the at least one deformable member in the annular connection portion; wherein when the first detector detects none of the breast milk inside the nipple passage, the first detector enables the first air pump to inflate and deflate the at least one deformable member alternately to press and touch the breast.

21. The breast pump according to claim 1, further comprising a sound recorder adapted to record an infant sound and replay the infant sound to stimulate a pituitary gland of the user to secret prolatine or oxytocin and allow the mammary gland to produce the breast milk.

* * * * *